(12) United States Patent
Cohen et al.

(10) Patent No.: US 12,016,838 B2
(45) Date of Patent: Jun. 25, 2024

(54) STABILIZED PROTEIN-BOUND CANNABINOID COMPOSITIONS

(71) Applicant: IZUN PHARMACEUTICALS CORP., New York, NY (US)

(72) Inventors: Shmuel Cohen, Nehosha (IL); William Z. Levine, Jerusalem (IL); Shimon Lecht, Petach Tikva (IL)

(73) Assignee: DAY THREE LABS MANUFACTURING INC., Denver, CO (US)

( * ) Notice: Subject to any disclaimer, the term of this patent is extended or adjusted under 35 U.S.C. 154(b) by 255 days.

(21) Appl. No.: 16/492,142

(22) PCT Filed: Mar. 9, 2018

(86) PCT No.: PCT/IL2018/050278
§ 371 (c)(1),
(2) Date: Sep. 8, 2019

(87) PCT Pub. No.: WO2018/163187
PCT Pub. Date: Sep. 13, 2018

(65) Prior Publication Data
US 2021/0128519 A1    May 6, 2021

(51) Int. Cl.
| | | |
|---|---|---|
| A61K 47/50 | (2017.01) | |
| A61K 31/05 | (2006.01) | |
| A61K 31/352 | (2006.01) | |
| A61K 47/12 | (2006.01) | |
| A61K 47/42 | (2017.01) | |
| A61K 47/64 | (2017.01) | |

(52) U.S. Cl.
CPC ............ *A61K 31/352* (2013.01); *A61K 31/05* (2013.01); *A61K 47/12* (2013.01); *A61K 47/42* (2013.01); *A61K 47/64* (2017.08); *A61K 47/643* (2017.08)

(58) Field of Classification Search
CPC .................................................... A61K 47/50
See application file for complete search history.

(56) References Cited

U.S. PATENT DOCUMENTS

| | | | |
|---|---|---|---|
| 4,933,363 A | 6/1990 | ElSohly | |
| 6,383,513 B1 * | 5/2002 | Watts | A61P 25/04 424/455 |
| 6,630,507 B1 | 10/2003 | Hampson | |
| 6,730,330 B2 | 5/2004 | Whittle | |
| 7,622,140 B2 | 11/2009 | Whittle | |
| 7,790,400 B2 | 9/2010 | Jehanli | |
| 8,445,034 B1 | 5/2013 | Coles | |
| 2012/0196873 A1 | 8/2012 | Nolte et al. | |

FOREIGN PATENT DOCUMENTS

| | | |
|---|---|---|
| GB | 2404023 | 1/2005 |
| KR | 20010052072 | 6/2001 |
| WO | 2010/124280 | 10/2010 |
| WO | 2013165251 | 11/2013 |
| WO | 2017137992 | 8/2017 |

OTHER PUBLICATIONS

"Chemical Characteristics—The Olive Oil Source." Accessed Nov. 29, 2021. First available to public on: Feb. 15, 2010. Available from: <https://www.oliveoilsource.com/page/chemical-characteristics>. (Year: 2010).*
Analysis of Cannabinoids in Hemp Seed Oils by HPLC using PDA detection, perrkin elmer, 2015.
Mark J. Pletcher et al.; "Association Between Marijuana Exposure and Pulmonary Function Over 20 Years" Jan. 11, 2012, JAMA vol. 307, No. 2 pp. 173-181.
Timna Naftali et al.; "Treatment of Crohn's Disease with Cannabis: An Observational Study" Aug. 2011, IMAJ vol. 13, pp. 455-457.
Robert Melamede; "Cannabis and tobacco smoke are not equally carcinogenic" Harm Reduction Journal, Oct. 18, 2005, pp. 1-4.
Donald E. Greydanus et al Marijuana, current concepts, Fontiers in Public Health Oct. 10, 2013, pp. 1-17.
Rudolf Brenneisen; "Chemistry and Analysis of Phytocannabinoids and other Cannabis Constituents"; Chemistry of Cannabis Constituents; from Forensic Science and Medicine: Marijuana and the Cannabinoids, Chapter 2, pp. 17-49, 2007; Edited by M.S. ElShohly, Humana Press Inc., Totowa, New Jersey.
S. Casano; "Variations in Terpene Profiles of Different Strains of Cannabis sativa L." IHC Seminar: A New Look at Jort Plants, Acta Hort, 925 pp. 115-122, 2011.
DeBacker et al.; Innovative development and validation of an HPLC/DAD method for the qualitive and quantitive determination of major cannabinoids in cannabis plant material; Journal of Chromatography B, 877 (2009), pp. 4115-4124.
European Search Report dated Nov. 24, 2017, for corresponding application No. 15764519.3 filed Oct. 14, 2016.
Grotenhermen F., Clinical Pharmacokinetics of Cannabinoids, Journal of Cannabis Therapeutics, vol. 3, No. 1, Jan. 31, 2003, pp. 3-51.
Haque S J, Poddar M, Interactions of cannabinoids with bovine serum albumin, Bioscience reports vol. 4, Mar. 31, 1984, pp. 239-243. (abstract only).
Kratz F. Albumin as a drug carrier: Design of prodrugs, drug conjugates and nanoparticles, Journal of Controlled Release, vol. 132, Jun. 30, 2008, pp. 171-183.
Bojesen, I. N., & Hansen, H. S. (2003). Binding of anandamide to bovine serum albumin. Journal of Lipid Research, 44 (9), 1790-1794, Jul. 1, 2003 (Jul. 1, 2003).

(Continued)

*Primary Examiner* — John S Kenyon
(74) *Attorney, Agent, or Firm* — JMB DAVIS BEN-DAVID (57) ABSTRACT

A method for producing a fatty acid-cannabinoid-plasma protein (FCP) composition, the method comprising: contacting a plasma protein or a peptide portion thereof with a supplemental fatty acid composition comprising at least one fatty acid; and contacting the plasma protein or portion thereof with a cannabinoid composition comprising at least one cannabinoid, such that a combined composition is prepared, which comprises a FCP complex in which the at least one fatty acid and the at least one cannabinoid is bound to the plasma protein or portion thereof.

19 Claims, 6 Drawing Sheets

(56) References Cited

OTHER PUBLICATIONS

Orsavova, J., Misurcova, L., Ambrozova, J. V., Vicha, R., & Mlcek, J. (2015). Fatty acids composition of vegetable oils and its contribution to dietary energy intake and dependence of cardiovascular mortality on dietary intake of fatty acids. International Journal of Molecular Sciences, 16(6), 12871-12890. Jun. 5, 2015 (Jun. 5, 2015).

Elmes, M. W., et al.(2015). Fatty acid-binding proteins (FABPs) are intracellular carriers for delta 9-etrahydrocannabinol (THC) and cannabidiol (CBD). Journal of Biological Chemistry, 290 (14), 8711-8721., Feb. 9, 2018 (Feb. 9, 2018).

* cited by examiner

STABILIZED PROTEIN-BOUND CANNABINOID COMPOSITIONS

CROSS-REFERENCE TO RELATED APPLICATIONS

This is the U.S. National Stage of International Patent Application No. PCT/IL2018/050278 filed on Mar. 9, 2018, which was published in English under PCT Article 21(2), and which in turn claims the benefit of U.S. Provisional Patent Application No. 62/469,022 filed on Mar. 9, 2017.

BACKGROUND

Cannabinoids are compounds active on cannabinoid and other receptors in humans. Cannabinoids of plant origin, also known as phyto-cannabinoids, are abundant in plants of the *Cannabis* genus. One known cannabinoid which is present in relatively high concentrations in *Cannabis sativa* is tetrahydrocannabinol-acid (THCA) or its decarboxylated product tetrahydracannabinol (THC). THC has been found to have psychoactive effects, analgesic effects, and antioxidant effects and to increase appetite.

Smoking medical *cannabis*, although proven to be beneficial in certain indications, has disadvantages. However, the amounts of active ingredients in the part of the plant being smoked may differ from plant to plant. As a result, a patient treated using medical *cannabis* may lack control over proper dosing of active cannabinoids.

Another disadvantage of smoking medical *cannabis* is the negative impact of some of the constituents of *cannabis* smoke. The smoke from the plant matter may contain carcinogens in addition to the desired cannabinoids, and heavy *cannabis* use through smoking has been associated with accelerated pulmonary decline.

Aqueous compositions of cannabinoids would allow for preparation of quality controlled, accurately dosed pharmaceutical compositions for administration and rapid absorption by humans.

SUMMARY

Embodiments of the invention provide improved compositions comprising cannabinoids. Methods for making such compositions are also provided herein. In particular, the compositions described herein below are stabilized when in an aqueous composition. The stabilization of the compositions may be determined, by way of example, by observing the stability of the color of the compositions and/or rate of cannabinoid degradation and/or preservation of bioactivity. An "aqueous" composition as used herein is a composition having a liquid medium that is at least 50% water. An "aqueous" solution as used herein is a solution in which the solvent is at least 50% water.

According to one aspect of the disclosure, there is provided a method for producing a stabilized fatty acid-cannabinoid-plasma protein ("FCP") composition, the method comprising: contacting a plasma protein with a supplemental fatty acid composition comprising at least one fatty acid; and contacting the plasma protein with a cannabinoid composition comprising at least one cannabinoid. Optionally, the fatty acid comprised in the supplemental fatty acid composition provides fatty acid in addition to fatty acid that may be comprised in the cannabinoid composition or may already be complexed with the plasma protein. In an embodiment of the disclosure, at least a portion of, most of, or essentially all of, the plasma protein in the FCP composition produced in accordance with the above method are non-covalently bound to a fatty acid and a cannabinoid, resulting in the formation of a FCP complex. Optionally, the non-covalent binding is a protein-ligand interaction. Optionally, the non-covalent binding is characterized by non-specific lipophilic and polar interactions, by way of example with hydrophobic protein pockets in the plasma protein.

In an embodiment of the disclosure, contacting the plasma protein with the supplemental fatty acid composition comprises mixing a composition comprising the plasma protein with the supplemental acid composition and incubating the mixture. Optionally the incubation is at between 25 degrees Celsius (deg. C.) and 40 deg. C., at about 25 deg. C., at about 30 deg. C., about 37 deg. C. or about 40 deg. C. Optionally, the incubation has a duration of between 30 minutes and 2 hours, about 30 minutes, about 1 hour, or about 2 hours. Optionally, the incubation is in a hydroalcoholic medium in which the initial alcohol concentration of the mixture is between 2% and 10%, or about 5%. Optionally, the alcohol is ethanol.

In an embodiment of the disclosure, contacting the plasma protein with the cannabinoid composition comprises mixing a composition comprising the plasma protein with the cannabinoid composition and incubating the mixture. Optionally the incubation is at between 25 degrees Celsius (deg. C.) and 40 deg. C., at about 25 deg. C., at about 30 deg. C., about 37 deg. C. or about 40 deg. C. Optionally, the incubation has a duration of 10 to 24 hours, and 16 to 18 hours. Optionally, the incubation is in a hydroalcoholic medium in which the initial alcohol concentration of the mixture is between 16% and 30%, or about 20%. Optionally, the alcohol is ethanol.

In an embodiment of the disclosure, the method further comprises retaining a plasma protein fraction from a filtration or sieving of the FCP composition, wherein the retained plasma proteins fraction comprises at least one fatty acid and at least one cannabinoid.

In an embodiment of the disclosure, following the filtration or sieving, at least 80%, 90% or essentially all of the THC comprised in the fatty acid-cannabinoid-plasma protein composition, and at least 80%, 90%, or essentially all of the fatty acid comprised in the fatty acid-cannabinoid-plasma protein composition, are bound to a plasma protein.

In an embodiment of the disclosure, the FCP composition is provided in a solution comprising water, and optionally a water-miscible, non-aqueous solvent. In an embodiment of the disclosure, the FCP composition is freeze-dried or dried.

In an embodiment of the disclosure, the supplemental fatty acid composition comprises the at least one fatty acid, a water-miscible, non-aqueous solvent, and optionally water. Optionally, the non-aqueous solvent is ethanol. Optionally, the fatty acid composition consists of the at least one fatty acid.

In an embodiment of the disclosure, the cannabinoid composition comprises a *cannabis* extract. The *cannabis* extract may be a purified *cannabis* extract depleted in non-cannabinoid extract constituents, by way of example proteins, lipids, or fatty acids. Optionally, the purified *cannabis* extract is enriched in cannabinoids. In an embodiment of the disclosure, the cannabinoid composition is a solution comprising at least one cannabinoid, a water-miscible non-aqueous solvent, and optionally water.

In an embodiment of the disclosure, the water-miscible non-aqueous solvent is ethanol.

A fatty acid is a carboxylic acid with a hydrocarbon tail. In an embodiment of the disclosure, the at least one fatty acid comprises one or a mixture of two or more of: long chain length fatty acids (13 or more carbons), short chain length fatty acids (up to 13 carbons); triglycerides; polyisoprenoids, or surfactants. In an embodiment of the disclosure, the at least one fatty acid comprises linoleic acid. In another embodiment the at least one fatty acid consists of linoleic acid.

Optionally, the at least one cannabinoid comprises one of or a combination of two or more of a cannabinoid selected from the group consisting of: tetrahydracannabinol-acid (THCA) or its decarboxylated product tetrahydracannabinol (THC) and cannabidiolic acid (CBDA) or its decarboxylated product cannabidiol (CBD), cannabidiolic acid (CBDA), cannabinol (CBN), cannabigerol (CBG), tetrahydrocannabivarin (THCV), cannabigerolic acid CBGA and cannabichromene (CBC). Alternatively or additionally, the group may comprise synthetic cannabinoids such as HU-210, WIN 55,212-2 and JWH-133.

As used herein, a plasma protein refers to proteins that are known to serve as transport vehicles in the bloodstream, by way of example for a variety of hydrophobic compounds, including fatty acids. The plasma protein may be derived or purified from blood plasma, or be a recombinant protein produced in a plant, bacteria, a cell line or other microorganism. The plasma protein is optionally selected from: an albumin, a lipoprotein, a glycoprotein, and α, β, and γ globulins, and mixtures thereof. The plasma protein may incorporate a complete plasma protein or a peptide comprising a portion of a plasma protein. The portion of the plasma protein may comprise a portion which adsorbs a cannabinoid. A plasma protein may be a variant of a naturally occurring plasma protein.

In an embodiment of the disclosure, the FCP composition comprises the at least one fatty acid in sufficient amount in to essentially prevent color alteration of the stabilized composition during at least 1 hour or at least 24 hours. In more preferred embodiments the prevention is for at least 4 months.

In an embodiment of the disclosure, the method comprises: (1) pretreating the plasma protein with the supplemental fatty acid composition to produce a fatty acid-plasma protein composition; and (2) combining the fatty acid-plasma protein composition with the cannabinoid composition to produce a FCP composition.

Alternatively, the method comprises: (1) pretreating the plasma protein with the cannabinoid composition to produce a cannabinoid-plasma protein composition; and (2) combining the cannabinoid-plasma protein composition with the supplemental fatty acid composition to produce a FCP composition.

Alternatively, the method comprises: (1) combining the supplemental fatty acid composition with the cannabinoid composition to produce a supplemental fatty acid-cannabinoid composition and (2) contacting the plasma protein with the supplemental fatty acid-cannabinoid composition to produce a FCP composition.

According to an embodiment of the disclosure, the at least one cannabinoid is not derived from a *cannabis* plant.

According to an embodiment of the disclosure, at least a portion of the at least one fatty acid is not derived from a *cannabis* plant.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labelled with a same numeral in all the figures in which they appear.

DETAILED DESCRIPTION

It has long been recognized that *cannabis* resin and herbal *cannabis* as sources for cannabinoids lose potency during storage, the loss of potency being mainly due to loss (through degradation or otherwise) of the cannabinoids, such as THC.

Plasma proteins are known to serve as transport vehicles in the bloodstream for a variety of hydrophobic compounds, including fatty acids. By way of example, human serum albumin (HSA) is a primary transporter for delivering fatty acids to tissues and possesses numerous fatty acid binding sites. We have previously found that binding cannabinoids to plasma proteins improves stability of cannabinoids in aqueous compositions. In addition, when the source of the cannabinoids is plant material, the binding also helps separate the cannabinoids from undesirable impurities carried over from the plant material into the extracts used for preparing the bound cannabinoids. Typically, the binding process includes incubating cannabinoids and plasma protein together in solution under certain conditions to produce cannabinoid-protein complexes, then concentrating the cannabinoid-protein complexes and washing the complexes to remove undesirable materials that do not bind with the proteins, resulting in aqueous compositions enriched in the cannabinoid-protein complexes.

However, such aqueous compositions have been found to alter their coloration over time, indicating an instability and degradation of the compositions. This degradation might be associated with an undesirable loss of potency of the dissolved cannabinoids, similar to the recognized THC potency loss described above and may be further associated with plasma protein degradation.

We have surprisingly found that aqueous compositions comprising plasma protein and cannabinoids are more stable when the cannabinoids are provided using *cannabis* extract (for example *cannabis* smoke extract or *cannabis* vapor extract), rather than purified cannabinoids. Fatty acids, which are naturally found in *cannabis* extracts but typically depleted in purified cannabinoid preparations, were initially hypothesized to contribute to the improvement of the stabilization. We have found that adding fatty acids, by way of example linoleic acid, during production of FCP compositions comprising plasma protein and cannabinoids as described hereinbelow, stabilizes the resulting composition when stored in an aqueous medium and reduces cannabinoid degradation. Improved stability was, by way of example, demonstrated through reduction in degradation of cannabinoids, reduced appearance of cannabinoid degradation products, reduced sedimentation and reduced flocculation of the aqueous FCP composition. Improved stability was also demonstrated through controlled reduction in the degree of the biological activity of the cannabinoids in the aqueous PFC composition. The stabilized preparations are suitable, for example, for pharmaceutical preparations, such as but not limited to solutions for parenteral or intranasal delivery.

Figure 1:
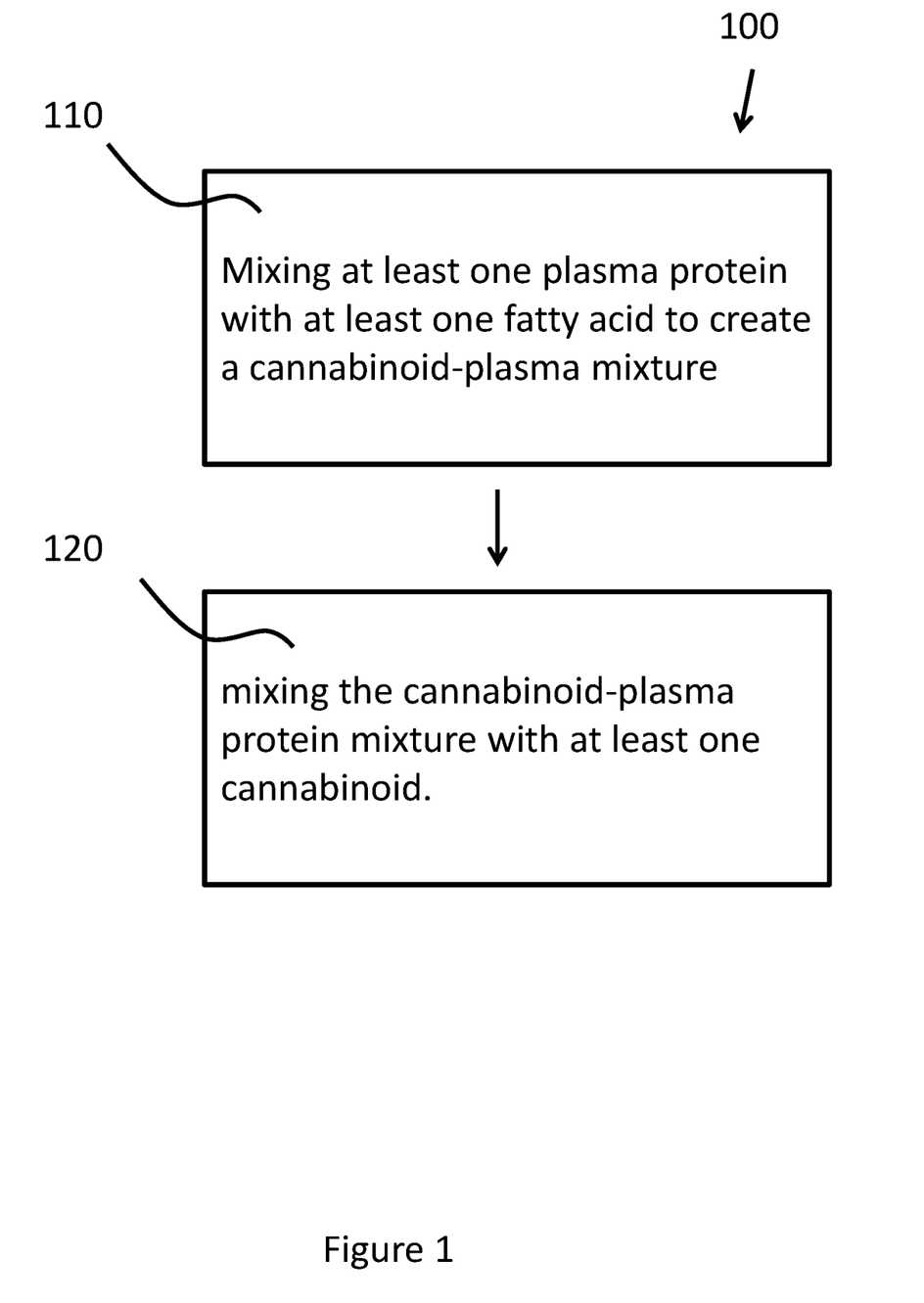
FIG. 1 shows a flow diagram depicting a process of preparing stabilized compositions of cannabinoids according to and embodiment of the disclosure.

FIG. 1 outlines steps in a method 100 of preparing an FCP composition according to an embodiment of the disclosure. The method 100 comprises: mixing at least one plasma protein with at least one fatty acid to create a fatty acid-plasma protein mixture (block 110); and mixing the fatty acid-plasma protein mixture with at least one cannabinoid (block 120).

Alternatively, the cannabinoids can be first mixed with the plasma protein and subsequently the cannabinoid-plasma protein mixture can be mixed with the fatty acids.

Figure 2:
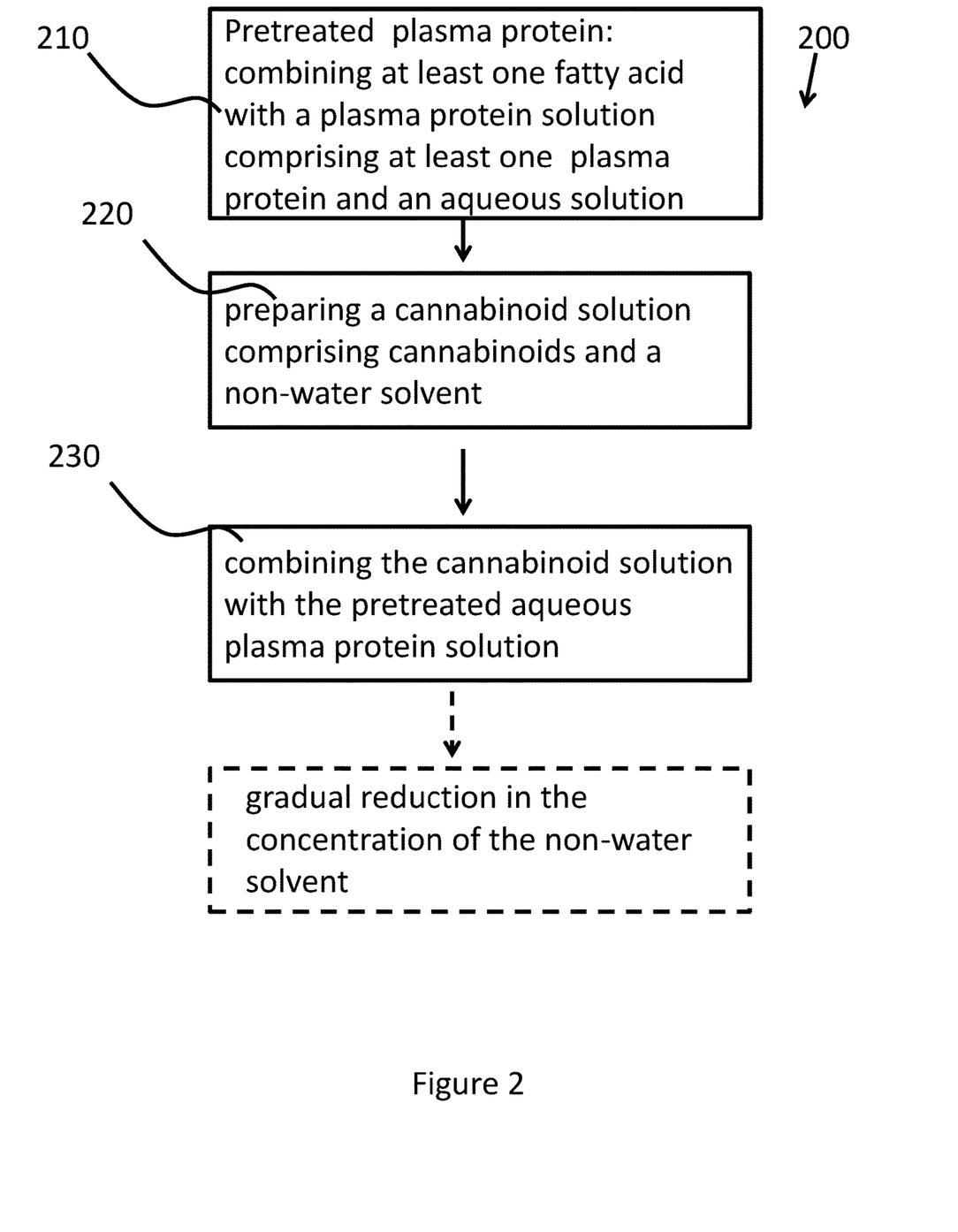
FIG. 2 shows a flow diagram depicting a process of preparing stabilized compositions of cannabinoids according to an embodiment of the disclosure.

FIG. 2 outlines steps in a method 200 of preparing an FCP composition according to an embodiment of the disclosure. The method 200 comprises: preparing a pre-treated plasma protein solution by adding a fatty acid into a plasma protein solution (block 210); and combining the pre-treated plasma protein solution with a cannabinoid solution comprising a cannabinoid and a non-water solvent (block 220). The FCP compositions may be in the form of an aqueous composition or may be freeze-dried or dried to a powder or lyophilized. In some embodiments the dried FCP composition is suspended in a medium such as saline solution for injection or intranasal application, for use for example as an analgesic.

Cannabinoids are typically provided in the form of an extract from a *cannabis* plant. Such extracts may contain varying amounts of fatty acids, depending at least partly on if or how much the extract is purified to remove non-cannabinoid compounds. However, in accordance with an embodiment of the disclosure, adding supplementary fatty acid in addition to any fatty acids already comprised in the *cannabis* extract serves to stabilize the fatty acid-plasma protein-cannabinoid mixture. Plasma protein preparations may also contain varying amounts of fatty acids already complexed to it, depending of if or how much the plasma protein is purified to remove other molecules. However, in accordance with and embodiment of the disclosure, adding supplementary fatty acid in addition to any fatty acids that may be already complexed to the plasma protein serves to stabilize the cannabinoid-plasma protein complex. Moreover, the stabilizing effect of the supplementary fatty acid persists even after the fatty acid-plasma protein-cannabinoid mixture is purified to remove "loose" fatty acids that are unbound to plasma protein.

Example 1: Preparation of Stabilized Compositions of Cannabinoids 1.1 Pretreatment of Albumin with Linoleic Acid Pure linoleic acid was dissolved in 50% ethanol to a concentration of 150 mM. 1 mL of the linoleic acid solution was added to 10 mL of a 100 mg/mL HSA (Human Serum Albumin) aqueous solution. The linoleic acid-HSA solution, which had an ethanol concentration of below 5%, was mixed for a minute and then incubated without stirring for 1 hour at 37° C.

1.2 Incubation of the Linoleic Acid-HSA Solution with THC

The linoleic acid-HSA solution prepared in step 1.1 was diluted in water to a tenth of the original concentration, so that the HSA concentration was reduced to 10 mg/mL and the ethanol concentration was reduced to about 0.5%.

A plant extract of THC of 94-95% purity was diluted in 100% ethanol to a THC concentration of 0.16 mg/mL. 25 mL of the 0.16 mg/mL THC solution was slowly added to 100 mL of the diluted linoleic acid-HSA solution prepared in this step, and incubated for 16-18 hours at 30° C., in an open container to facilitate evaporation of the ethanol, and protected from light. Following incubation, the THC-linoleic acid-HSA composition had a volume of about 100 mL, a HSA concentration of about 10 mg/mL, and a THC concentration of about 0.4 mg/mL.

During the incubation, the concentration of alcohol in the solution gradually decreased and the volume of the linoleic acid-HSA-THC composition diminished from the initial volume of about 125 ml to about 100 mL.

THC gradually binds to the albumin during incubation. As a result, the concentration of free THC gradually decreases, and the concentration of ethanol can accordingly decrease during the incubation, while mitigating the danger of THC coming out of solution and coalescing into sediment or an oil. By way of example, given an initial THC concentration 0.32 mg/mL, having the pre-incubation ethanol concentration be above 16.7% helps prevent THC from coming out of solution. A THC solution of a higher initial concentration may require a higher initial ethanol concentration for the THC to remain in solution. However, the ethanol should be at an initial concentration of below about 30% to prevent precipitation of albumin. Similar adjustments may be required in manufacture of other cannabinoid-albumin complexes, such as CBD complexes.

1.3 Purification of the Albumin Bound to THC and Linoleic Acid

After the incubation, most of the THC and fatty acid unbound to HSA was removed by dialysis filtration with wash cycles by DI (deionized water) filtration in a Cogent μscale device of Merck, using Pellicon XL50 cassettes (Ultracel) having a pore size of 10 kD (Pellicon XL Ultra filtration Module Ultracel 10 kDa 0.005 m2, catalog #PXCO10c50). Subsequently, the linoleic acid-THC-HSA complexes were concentrated with the Cogent device from 100 ml to 50 ml. Three 300 mL water washes were performed on the concentrated linoleic acid-THC-HSA complex sample and finally the washed sample was concentrated to a volume of about 20 mL. Samples were drawn from several of the purifications stages to monitor the levels of cannabinoids and plasma protein and determine that three washings sufficed to provide adequate amount of tightly bound complexes.

1.4 Preparation of Control

Control THC-HSA compositions ("−L compositions") free of added linoleic acid, were prepared as in steps 1.1 to 1.3 above, but without the step of the addition of linoleic acid in step 1.1. The final purified and concentrated THC-HSA composition contained albumin at a concentration of 66 mg/mL and THC at a concentration of 1790 ug/mL.

1.5 Comparison of Linoleic Acid-THC-Albumin (+L) Composition to THC-Albumin (−L) Composition Vials containing final purified and concentrated control THC-albumin complexes ("−L", product of step 1.4 above) and separate vials containing final purified and concentrated linoleic acid-THC-albumin complexes ("+L", product of step 1.3 above) were stored under identical conditions, at 4° C. and in the dark.

Table 1 summarizes the appearances of the THC-albumin compositions in the vials over time.

TABLE 1

|  | Control THC - albumin composition (−L) | linoleic acid-THC- albumin composition (+L) |
|---|---|---|
| Albumin concentration | 66.0 mg/mL | 62.9 mg/mL |
| THC concentration | 1.790 | 1.771 |
| THC:Albumin ratio (by weight) | 0.027:1 | 0.028:1 |
| Solution color at time = 0 | Milky white | Milky white |
| Solution color at time = 24 h | Milky brownish | unchanged |
| Solution color at time = 48 h | Brownish gray | unchanged |
| Solution color at time = 5 days | Darkens | unchanged |
| Solution color at time = 2 weeks | Strong brown | unchanged |
| Solution color at time = 3 weeks | Darkens | unchanged |
| Solution color at time = 4 months | Darkens | unchanged |

Figure 3A:
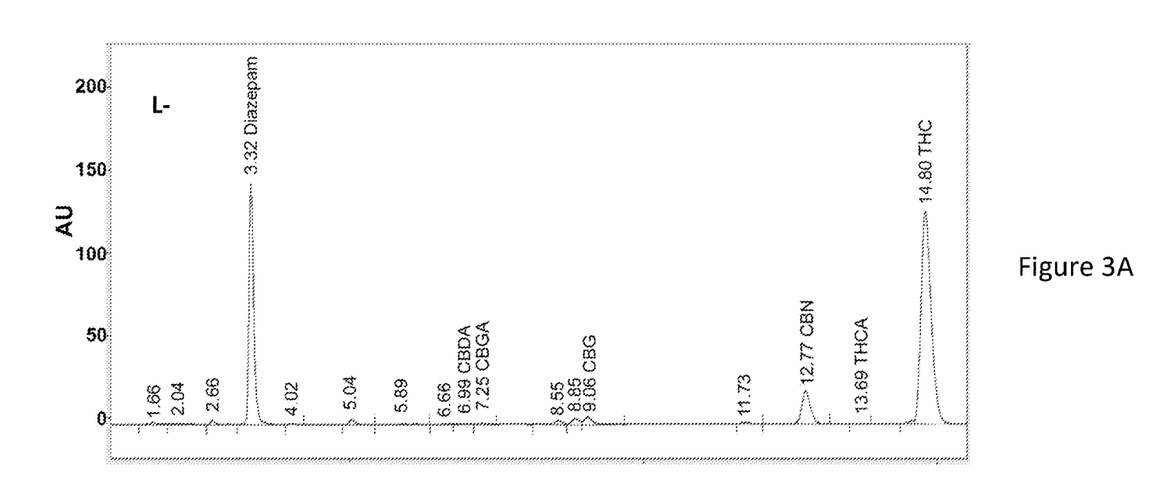
FIG. 3A depicts chromatograms of an FCP composition prepared from THC, albumin and linoleic acid (+L compositions), produced in accordance with an embodiment of the disclosure.
Figure 3B:
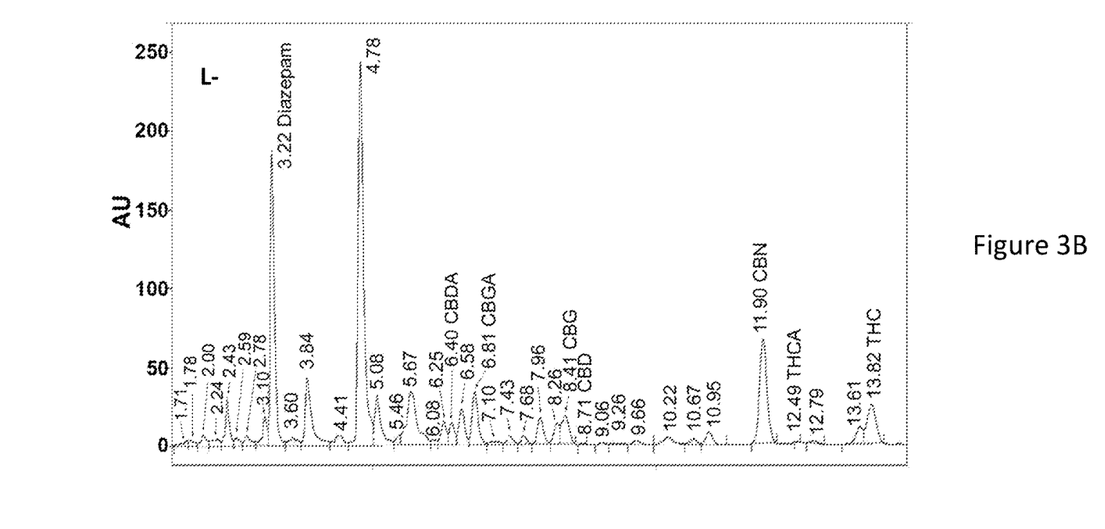
FIG. 3B depicts chromatograms of cannabinoid-plasma protein prepared from THC and albumin (without linoleic acid) as controls (−L compositions)
Figure 4A:
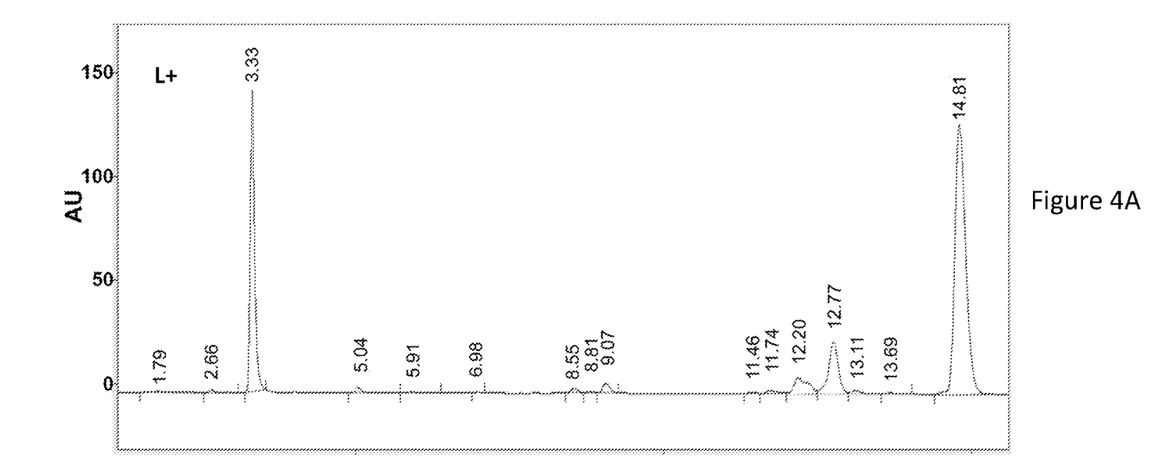
FIG. 4A depicts a chromatogram of the +L composition shown in FIG. 3A, after 4 months of storage.
Figure 4B:
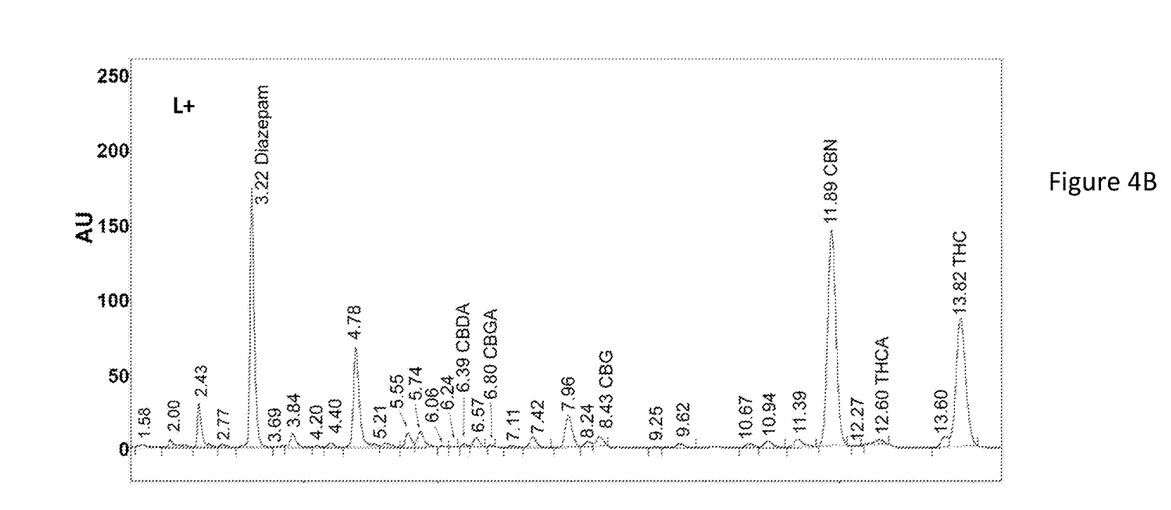
FIG. 4B depicts a chromatogram of the −L composition shown in FIG. 3B, after 4 months of storage.

The +L, and the −L compositions were each treated to unbind the cannabinoid from the albumin. The unbound cannabinoid was quantitatively and qualitatively determined by HPLC analysis and the albumin was separately measured, at the time of preparation and 4 months later. The chromatograms of the −L composition at 0 months (time of preparation) and 4 months after preparation are shown in FIGS. 3a and 3b, respectively. The chromatograms of the +L composition at 0 months and 4 months after preparation are shown in FIGS. 4a and 4b, respectively. Note that the chromatograms at 0 months of the −L composition (FIG. 3a) and the +L composition (FIG. 4a) are essentially identical, as is expected. By contrast, at 4 months, the chromatograms of the −L composition (FIG. 3b) and the +L composition (FIG. 4b) have substantial differences, with the −L chromatogram exhibiting more peaks, representing impurities arising from increased degradation in the −L composition.

Table 2 summarizes quantitative results from the HPLC analysis.

TABLE 2

|  | 21 Jul. 2016 0 months | | 11 Dec. 2016 4 months | |
|---|---|---|---|---|
| Analyte | µg/mL in +L | µg/mL in −L | µg/mL in +L | µg/mL in −L |
| Δ⁹-THC | 1789.809 | 1770.59 | 1089 | 340 |

Biological activity of THC in the −L and +L compositions were also compared, in order to assess THC stability in the respective compositions. Murine macrophage cell line RAW264.7 (obtained from the American Type Culture Collection) was transduced with an NF-κB luciferase reporter construct. Lipopolysaccharide (LPS) was used to induce the NF-κB luciferase reporter in the transduced RAW264.7 cells, and the test compositions (−L and +L compositions) were added to test for their ability to inhibit LPS-induced luciferase expression. Calcein AM (acetomethoxy derivate of calcein) was used as a fluorescent dye to determine RAW264.7 cell number for normalization. As luminescence in the model is correlated to activation of NF-κB, inhibition of expression can be determined by correlation with inhibition of luminescence.

It has previously been shown using the RAW264.7 NF-κB luciferase reporter assay that the expression of the NF-κB luciferase reporter is inhibited by administration of albumin-bound THC.

Figure 5A:
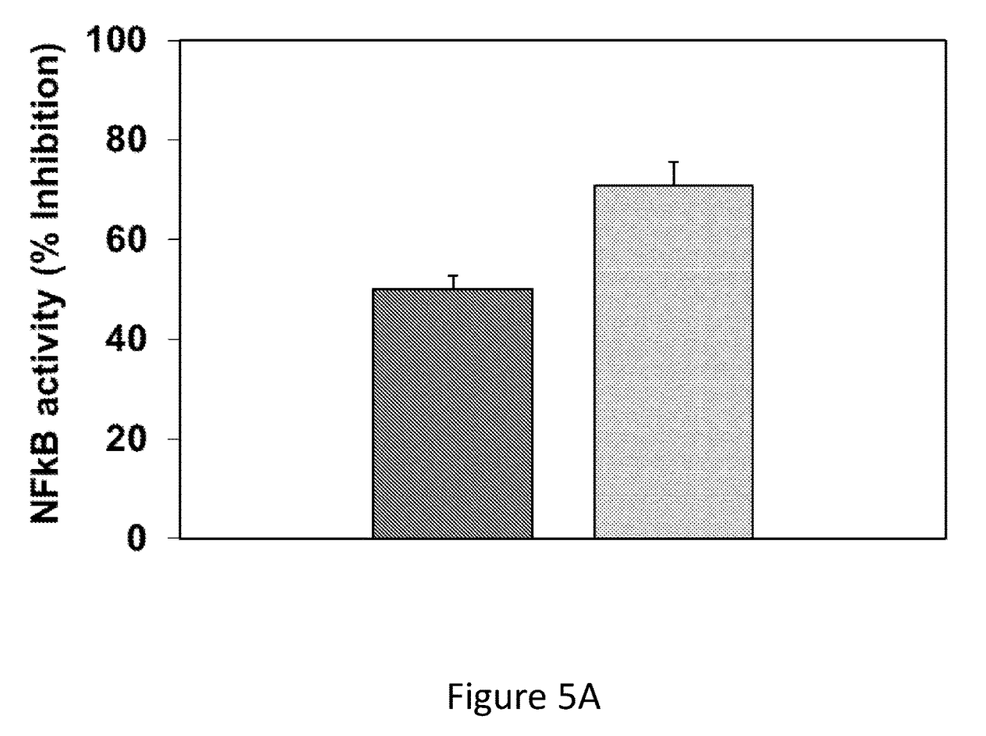
FIG. 5A shows the results of NF-κB luciferase reporter assays testing the biological activity of THC in the +L and −L composition after a week of storage.

Reference is made to FIG. 5A. The transduced RAW264.7 cells were treated with one of two test compositions: +L composition or the −L composition, after 1 week of storage in the dark, sealed, at 4° C. For each test composition, a sufficient amount of the test composition was added to the culture medium, such that, if the test composition was added to the culture at the time to test composition was initially made, prior to storage, the cells would have been exposed to THC at a concentration of 1 µg/ml. For both test compositions, luminescence was compared to a negative control in which luciferase expression was induced with LPS, without a test composition. It was found that administration of one-week-old −L composition inhibited LPS-induced luciferase expression by 50% compared to negative controls. By contrast, the +L composition inhibited luciferase expression by 70.9% compared to negative controls, indicating that the addition of linoleic acid improved stability of albumin-bound THC, and retarded degradation of the THC during the week of storage.

Figure 5B:
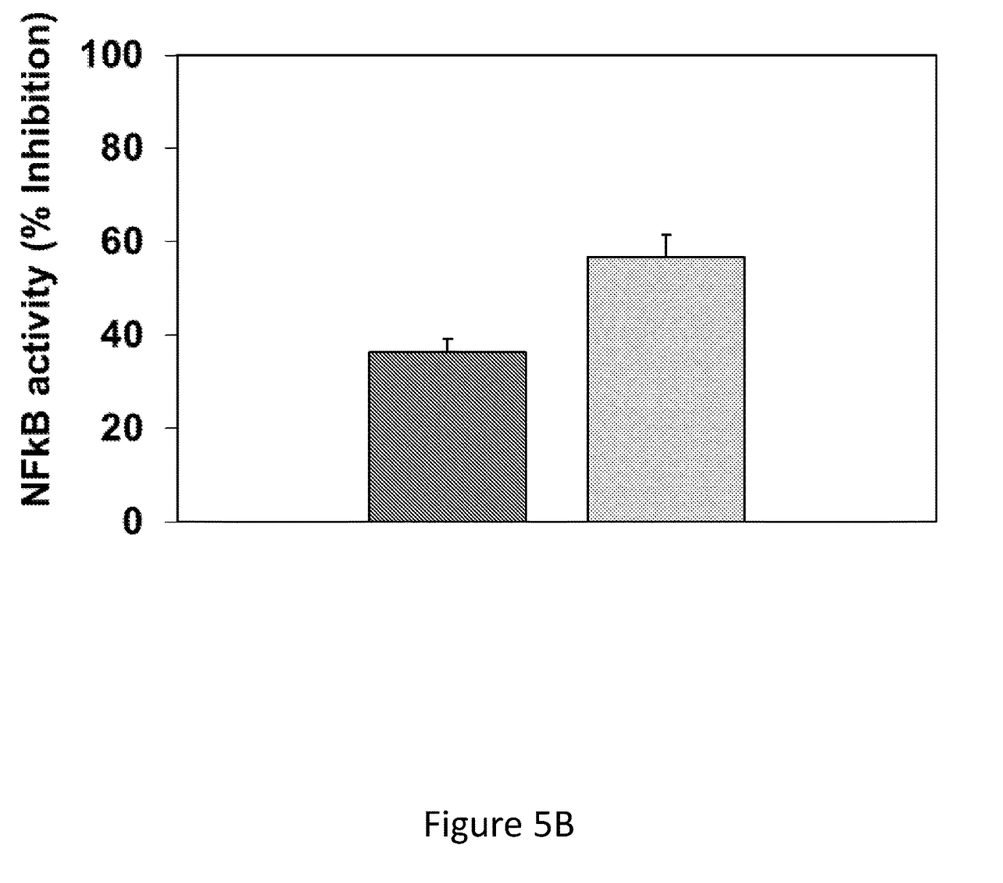
FIG. 5B shows the results of NF-κB luciferase reporter assays testing the biological activity of THC in the +L and −L composition after a month of storage.

Reference is made to FIG. 5B. The +L and −L compositions were similarly tested after 1 month of storage under the same conditions. It was found that administration of one-month-old −L composition inhibited expression of NF-κB luciferase reporter by 36.4% compared to negative controls. By contrast, the +L composition inhibited luciferase expression by 56.8% compared to negative controls, indicating that the addition of linoleic acid improved stability of albumin-bound THC, and retarded degradation of the THC during the month of storage.

As discussed by way of example in Example 1, step 1.2, in some embodiments, the method 200 further comprises 240 incubating the stabilized cannabinoid composition. The incubating comprises allowing gradual reduction in the concentration of the non-water solvent in the stabilized cannabinoid composition over time. The concentration reduction may be sufficiently slow to essentially minimize or prevent precipitation of cannabinoids out of the stabilized cannabinoid composition.

Preferably, as described by way of example in Example 1 step 1.1, the 210 preparing a pre-treated plasma protein solution further comprises incubating the fatty acid with the plasma protein solution. Preferably, the solution is moved as little as possible to minimize upsetting the complexation process, similar to the procedure followed in adsorbing peptides onto plastic vessels in ELISA analyses.

As discussed by way of example in step 1.3 of Example 1, the method may comprise retaining a plasma protein fraction from a filtration or sieving of the stabilized cannabinoid composition for enriching FCP complexes in solution, wherein the retained plasma proteins fraction comprises cannabinoids bound to the plasma protein and at least one fatty acid.

The at least one cannabinoid may be selected from the group consisting of: tetrahydracannabinol-acid (THCA) or its decarboxylated product tetrahydracannabinol (THC) and cannabidiolic acid (CBDA) or its decarboxylated product cannabidiol (CBD), cannabidiolic acid (CBDA), cannabinol (CBN), cannabigerol (CBG), tetrahydrocannabivarin (THCV), cannabigerolic acid CBGA and cannabichromene (CBC), and combinations thereof. Alternatively or additionally, the group may comprise synthetic cannabinoids such as HU-210, WIN 55,212-2 and JWH-133. In some embodiments the cannabinoids are provided as plant extract/s. One or more of the plant extracts may comprise a mixture of terpenes and cannabinoids, creating a bouquet of cannabinoid terpenes and optionally additional compounds, which may bind together to one or more albumin-linoleic acid complexes. The at least one plasma protein may comprise Human Serum Albumin (HSA).

The at least one fatty acid may comprise linoleic acid. However, other fatty acids may be as capable of stabilizing the THC-plasma protein or have at least similar capability. Such fatty acids are also considered as within the scope of the methods and compositions made thereof.

As indicated in Table 1 and Table 2, despite no discernible change in the color of the composition from its time of preparation there may be some degradation of THC in the composition during that time. Indeed, the amount of THC may considerably drop over an extended period such as 4 months; and earlier use of the composition may be preferable; however, the stability of THC in THC-albumin compositions is nevertheless profoundly improved by the presence of linoleic acid associated with the THC-albumin complex.

In some embodiments most of the at least one fatty acid is not derived from a cannabinoid plant. Some cannabinoid plants and in particular, some parts of these plants, such as the fruit or seeds, may have appreciable amounts of fatty acids. However, the cannabinoids are typically provided as purified extracts containing at least or more than 90% cannabinoids. Although the cannabinoid purified extracts may contain fatty acid traces from the cannabinoid plant source, adding supplemental fatty acids may improve stabilization of the cannabinoid-plasma protein-fatty acid compositions as described above.

Nevertheless, in some other embodiments the majority of fatty acids may be from a cannabinoid plant. In such cases the fatty acids are not merely minor compounds in the cannabinoid extracts, but rather are supplements to the cannabinoid extracts. At present we hold that the particular source of the fatty acids is insignificant to the observed stability effect.

According to an embodiment of the disclosure, a stabilized cannabinoid-plasma protein-fatty acid composition comprises: a plasma protein pre-treated with at least one fatty acid, and cannabinoids.

The pre-treatment may involve providing the plasma protein in an aqueous solution and the fatty acid in a suitable solvent which is miscible with water such as ethanol and mixing together the two solutions. The source of the fatty acids used for pre-treatment may be at least in part from a cannabinoid plant, but is generally not from cannabinoid plants. The source of the fatty acids in the composition is generally not from cannabinoid plants.

The cannabinoids are typically provided as an extract, in particular an extract of cannabinoids from cannabinoid plants, wherein the solvent is a non-aqueous solvent which is miscible with water such as ethanol. The extract may contain traces of fatty acids, but these traces are not used for pre-treatment. In some embodiments the concentration of the at least one fatty acid in the composition is selected to provide the stabilized cannabinoid-plasma protein-fatty acid composition with a color that is different from a color of a non-stabilized cannabinoid composition comprising: the cannabinoids at the same concentration as in the stabilized composition, and the at least one plasma proteins at the same concentration as in the stabilized composition, wherein the stabilized cannabinoid composition and the non-stabilized cannabinoid composition are concomitantly prepared and are concomitantly measured thereafter. In other embodiments the concentration the at least one fatty acid in the composition is selected to substantially retard the degradation of the cannabinoids in the composition, for example the degradation of THC, for example to retain at least 50% of the THC in the composition over a 4-month period in a stabilizing environment e.g., under 10° C. and in the dark.

In certain embodiments of the disclosure, the concentration of the fatty acids, relative to the concentration of cannabinoids, is such that if there is any color alteration of the stabilized composition, the color alteration is imperceptible to the naked eye. The color change may be tested by preparing a fresh sample of the composition and comparing the colors of the fresh sample to those of a sample made under the same conditions and concentrations as in the fresh sample but stored for stability testing.

There is therefore provided, in an embodiment of the disclosure, A method for producing a fatty acid-cannabinoid-plasma protein (FCP) composition, the method comprising: contacting a plasma protein or a peptide portion thereof with a supplemental fatty acid composition comprising at least one fatty acid; and contacting the plasma protein or portion thereof with a cannabinoid composition comprising at least one cannabinoid, such that a combined composition is prepared, which comprises a FCP complex in which the at least one fatty acid and the at least one cannabinoid is bound to the plasma protein or portion thereof. Optionally, at least one fatty acid comprises linoleic acid. Optionally, at least one fatty acid consists of linoleic acid. Optionally, the cannabinoid composition is essentially free of fatty acids.

In an embodiment of the disclosure, the method further comprises: purifying the combined composition to retain the plasma protein or portion thereof and to remove fatty acid or cannabinoids not bound the plasma protein or portion thereof, such that at least 80% of the fatty acids and at least 80% of the cannabinoids in the combined composition are bound to the plasma protein or portion thereof. Optionally, substantially all the fatty acids and substantially all the cannabinoids in the combined composition are bound to the plasma protein or portion thereof.

In an embodiment of the disclosure, the binding of the fatty acid and/or the cannabinoid to the plasma protein or portion thereof is a non-covalent binding. Optionally, the non-covalent binding is a protein-ligand interaction. Optionally, the non-covalent binding is characterized by non-specific lipophilic and polar interactions with hydrophobic protein pockets in the plasma protein or portion thereof.

In an embodiment of the disclosure, contacting the plasma protein or portion thereof with the supplemental fatty acid composition comprises mixing a composition comprising the plasma protein or portion thereof with the supplemental acid composition and incubating the mixture. Optionally, the incubation is at a temperature between 25 degrees Celsius (deg. C.) and 40 deg. C. Optionally, the incubation is in a hydroalcoholic medium. Optionally, the alcohol comprised in the hydroalcoholic medium is ethanol. Optionally, initial alcohol concentration of hydroalcoholic medium is between 2% and 10%.

In an embodiment of the disclosure, contacting the plasma protein or portion thereof with the cannabinoid composition comprises mixing a composition comprising the plasma protein or portion thereof with the cannabinoid composition and incubating the mixture. Optionally, the incubation is at a temperature between 25 degrees Celsius (deg. C.) and 40 deg. C. Optionally, the incubation is in a hydroalcoholic medium. Optionally, the alcohol comprised in the hydroalcoholic medium is ethanol. Optionally, initial alcohol concentration of hydroalcoholic medium is between 16% and 30%.

In an embodiment of the disclosure, the combined composition is provided in an aqueous medium. Optionally, the aqueous medium consists of water or a saline solution.

In an embodiment of the disclosure, the method further comprises drying or lyophilizing the combined composition.

In an embodiment of the disclosure, the at least one cannabinoid is one or a combination of two or more of the group consisting of: THCA, THC, CBDA, CBD, CBN, CBG, THCV, CBGA, CBC, HU-210, WIN 55,212-2 and JWH-133.

In an embodiment of the disclosure, the plasma protein or portion thereof is selected from the group consisting of: an albumin, a lipoprotein, a glycoprotein, and α, β, and γ globulins, and mixtures of one or more thereof. Optionally, the plasma protein or portion thereof is recombinant.

There is also provided an FPC composition produced using a method in accordance with an embodiment of the disclosure.

There is also provided a method for improving stability for a cannabinoid bound to a plasma protein, comprising producing the FCP composition using a method in accordance with an embodiment of the disclosure.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method for producing a fatty acid-cannabinoid-plasma protein (FCP) composition, the method comprising:
    contacting a plasma protein or a peptide portion thereof with a supplemental fatty acid composition consisting essentially of at least one fatty acid and a solvent; and
    contacting the plasma protein or portion thereof with a phytocannabinoid composition comprising at least one phytocannabinoid,
    such that a combined composition is prepared, which comprises a FCP complex in which the at least one fatty acid and the at least one phytocannabinoid is bound to the plasma protein or portion thereof; further comprising purifying the combined composition to retain the plasma protein or portion thereof and to remove fatty acid or phytocannabinoids not bound the plasma protein or portion thereof, such that at least 80% of the fatty acids and at least 80% of the phytocannabinoids in the combined composition are bound to the plasma protein or portion thereof.

2. The method of claim 1, wherein the at least one fatty acid comprises linoleic acid.

3. The method according to claim 1, wherein the FCP composition is free of fatty acids which are not bound by plasma protein.

4. The method according to claim 1, wherein the binding of the fatty acid and/or the phytocannabinoid to the plasma protein or portion thereof is a non-covalent binding.

5. The method according to claim 1, wherein contacting the plasma protein or portion thereof with the supplemental fatty acid composition comprises mixing a composition comprising the plasma protein or portion thereof with the supplemental acid composition and incubating the mixture.

6. The method according to claim 5, wherein the incubation is in a hydroalcoholic medium.

7. The method according to claim 6, wherein the alcohol comprised in the hydroalcoholic medium is ethanol.

8. The method according to claim 6, wherein initial alcohol concentration of hydroalcoholic medium is between 2% and 10%.

9. The method according to claim 1, wherein contacting the plasma protein or portion thereof with the cannabinoid composition comprises mixing a composition comprising the plasma protein or portion thereof with the cannabinoid composition and incubating the mixture.

10. The method according to claim 9, wherein the incubation is in a hydroalcoholic medium.

11. The method according to claim 10, wherein the alcohol comprised in the hydroalcoholic medium is ethanol.

12. The method according to claim 10, wherein initial alcohol concentration of hydroalcoholic medium is between 16% and 30%.

13. The method according to claim 1, wherein the combined composition is provided in an aqueous medium.

14. The method according to claim 13, wherein the aqueous medium consists of water or a saline solution.

15. The method according to claim 13, further comprising drying or lyophilizing the combined composition.

16. The method according to claim 1, wherein the at least one phytocannabinoid is one or a combination of two or more of the group consisting of: THCA, THC, CBDA, CBD, CBN, CBG, THCV, CBGA, and CBC.

17. The method according to claim 1, wherein the plasma protein or portion thereof is selected from the group consisting of: an albumin, a lipoprotein, a glycoprotein, and α, β, and γ globulins, and mixtures of one or more thereof.

18. The method according to claim 1 wherein the solvent of the supplemental fatty acid composition is an alcohol.

19. The method according to claim 18 wherein the alcohol is ethanol.

\* \* \* \* \*